(12) United States Patent
Allen

(10) Patent No.: US 9,823,211 B1
(45) Date of Patent: Nov. 21, 2017

(54) GAS CHARACTERIZATION SYSTEM HAVING A PRECONCENTRATOR

(71) Applicant: Maxim Integrated Products, Inc., San Jose, CA (US)

(72) Inventor: Dan G. Allen, Cupertino, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 206 days.

(21) Appl. No.: 14/670,839

(22) Filed: Mar. 27, 2015

Related U.S. Application Data

(60) Provisional application No. 62/047,686, filed on Sep. 9, 2014.

(51) Int. Cl.
*G01N 27/40* (2006.01)
*G01N 27/30* (2006.01)
*G01N 27/31* (2006.01)

(52) U.S. Cl.
CPC ........... *G01N 27/304* (2013.01); *G01N 27/31* (2013.01); *G01N 27/40* (2013.01)

(58) Field of Classification Search
CPC .... G01N 27/26–27/286; G01N 27/304; G01N 27/307; G01N 27/404–27/41

USPC ................. 204/409–412, 416–429, 431–432
See application file for complete search history.

(56) References Cited

U.S. PATENT DOCUMENTS

| | | | |
|---|---|---|---|
| 2006/0027465 A1* | 2/2006 | Nair | G01N 27/4074 205/781 |
| 2007/0012566 A1* | 1/2007 | Nair | G01N 27/4067 204/431 |

* cited by examiner

*Primary Examiner* — Bach Dinh
(74) *Attorney, Agent, or Firm* — Advent, LLP

(57) ABSTRACT

Disclosed herein are embodiments of a gas sensor system and methods of analyzing data therefrom. In embodiments, a gas sensor system includes one or more gas preconcentrator modules and one or more gas sensor modules. Each gas preconcentrator module includes a substrate that has a top surface having a gas adsorbent material attached to the top surface and has an electrical heater element for heating each preconcentrator module to release adsorb gases to the sensor. The gas sensor modules and the gas preconcentrator modules are in fluid communication with each other. The gas sensor modules responses are readout in parallel multiple times as the preconcentrators are heated yielding a 2-dimensional gas spectrum. The gas sensor output data is analyzed and compared to a library of known data to analyze the gas composition.

19 Claims, 15 Drawing Sheets

900A

900B

GAS CHARACTERIZATION SYSTEM HAVING A PRECONCENTRATOR

CROSS-REFERENCE TO RELATED APPLICATIONS

The present application claims the benefit under 35 U.S.C. §119(e) of U.S. Provisional Application Ser. No. 62/047,686, entitled GAS CHARACTERIZATION SYSTEM HAVING A PRECONCENTRATOR, filed Sep. 9, 2014. U.S. Provisional Application Ser. No. 62/047,686 is hereby incorporated by reference in its entirety.

BACKGROUND

A gas sensor is a subclass of chemical sensors that measures the concentration of gases in the vicinity of the sensor. A gas interacts with the sensor and provides a measure of the concentration of the gas based on a signal or property change created by the interaction. Gas sensors can include sensors based on measuring changes in electrical properties of the sensor, such as, but not limited to, metal oxide semiconductor sensors, polymer coating based sensors, carbon nanotube based sensors, and moisture adsorbing material based sensors. Other types of gas sensors can include sensors based on measuring other properties, such as, but not limited to, optical, acoustic, gravimetric, gas chromatograph, flame ionization, and calorimetric based sensors.

Generally, gas sensors are designed to detect a specific type of gas or class of gases. For example, there are specific gas sensors designed to have sensitivity to specific gases such as carbon monoxide, carbon dioxide, nitrous oxide compounds, ammonia, methane, sulfur dioxide, hydrogen sulfide, methanol, ethanol, and volatile organic compounds. The signal generated by the interaction of gases with a sensor is related to the total concentration of all types of gases that the sensor can detect. In other words, a gas sensor may not be discriminatory with respect to the different gases that the sensor is able to detect at selected operating conditions since the total signal generated is a function of the responses from all detected gases. Therefore, a common approach for gas sensors is to design a sensor to detect a specific type of gas while minimizing sensitivity to other types of gases, or to provide a means to separate gas species and measure one at a time.

For applications in mobile devices and consumer devices where the context varies greatly, it can be desirable for a gas sensor system to provide resolution sufficient to characterize or classify a gas or mixture of gases in order to determine the context, as a human does via its sense of smell. The value of an electronic nose for mobile and consumer applications is not limited to an analytical measurement of a particular gas concentration. Rather, it can be desirable to capture the signature or characteristics associated with a mixture of volatile organic for context identification or comparison. Various uses might include, but are not limited to, identification of a smell, an environment, or a combination of chemicals triggering another measurement or a report, validation of a material's authenticity or capturing a snapshot of particular smell or environment for data aggregation. In such applications, analytical grade measurements may not be necessary. However, the more characteristics of a gas mixture that can be measured, the better. For consumer and mobile applications, cost, size, speed of measurement and power consumption are also important. Common lab analytical equipment often does not meet desired specifications or budget. There is a need in the art for a compact, low cost, low power, rapid gas characterization system with resolution improved over individual or even simple arrays gas sensors. Improved sensitivity to trace concentrations may also be desirable.

An array of gas sensors with varied selective responses can provide a measure of chemical selectivity. For instance, for a given volatile organic compound (VOC), a metal oxide (MOX) gas sensor whose resistance varies with the concentration of combustible gas, has a particular temperature at which the response is maximum for a given gas. In theory, a temperature scan of a MOX sensor would identify a molecular species. However, many chemicals can have the same or similar temperature-dependent responsivities, so this kind of selectivity can have practical limits, especially where the sensor context (location, environment, etc.) varies widely.

In another example of an array, MOX sensors can be provided with different metal oxide materials. The different materials provide different responses to gases. However, yet again, many analytes or combinations of analytes may have similar and undifferentiated responses. Given an array with limited selectivity or resolution, another axis of resolution or selectivity is desired for characterization or classification of gas mixtures.

SUMMARY

A gas characterization system is described in this disclosure. In embodiments, the system includes one or more preconcentrator modules and one or more gas sensor modules. The preconcentrator modules and the gas sensor modules are in fluid communication with each other and a gas inlet port. Each preconcentrator module can include a substrate with an integral heater, and a surface on which is deposited a gas adsorbent. The gas adsorbent material is typically porous and capable of adsorbing gases that come in contact with the material, especially volatile organic compounds. An integral heater element of the preconcentrator can be used to increase the temperature of the preconcentrator to release adsorbed gases from the gas adsorbent material. Different adsorbed gases release at different temperatures, depending on boiling point (volatility) and affinity for the gas adsorbent material. The released gases can come into contact with the gas sensor modules and interact with the gas sensor modules, resulting in a change in a response from a baseline response for one or more of the gas sensor modules. The change in response is obtained and analyzed. As the temperature of the preconcentrator increases, the evolution of the change in response from the array of gas sensor modules can provide a two-dimensional (2D) characteristic response for a gas or mixture of gases for analysis or classification.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The Detailed Description is described with reference to the accompanying figures. The use of the same reference numbers in different instances in the description and the figures may indicate similar or identical items.

DETAILED DESCRIPTION

Overview

Figure 1A:
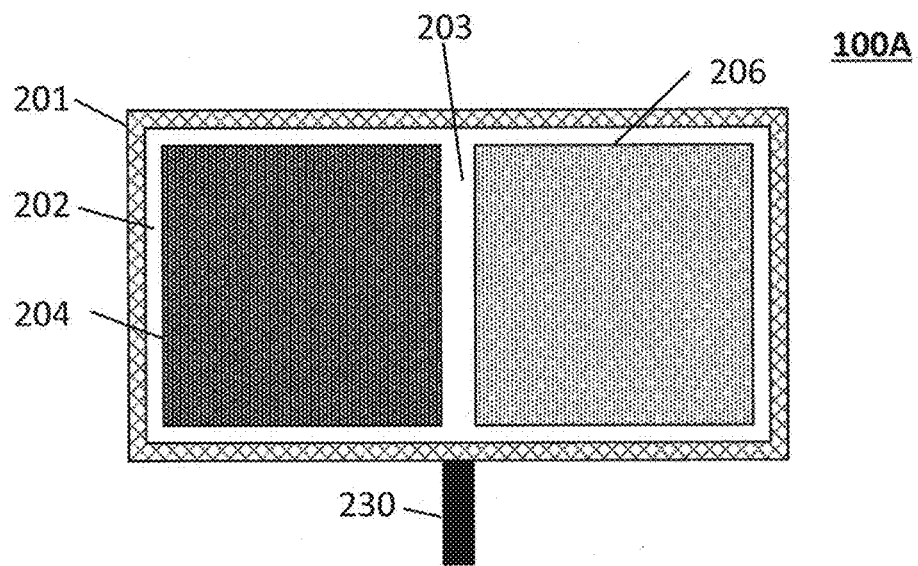
FIG. 1A illustrates a top view of a gas sensor module and preconcentrator module and showing an electrical line bundle for heaters, electrodes, and other lines, including read lines, in accordance with an embodiment of this disclosure.

Disclosed herein are various embodiments of a gas sensor system. In an embodiment, a gas sensor system includes one or more gas preconcentrator modules and one or more gas sensor modules. Each gas preconcentrator module can include a substrate that has an embedded heater element and surface having a gas adsorbent material attached thereto. The gas sensor modules and the gas preconcentrator modules may be in fluid communication (e.g., fluidically coupled) with each other. The gas sensor modules can provide a range of responses that varies according to some properties of the gas analyte. Some types of sensors, such as heated metal oxide gas sensors, may have limited chemical selectivity. Therefore, chemical separation can further improve the chemical resolution. In some embodiments, chemicals, such as volatile organic compounds (VOCs), can be separated according to volatility (e.g. boiling points).

When exposed to a mixture of VOCs, such as an item of food, or human breath, a preconcentrator can adsorb multiple VOC species. When heated, the smallest, lightest, most volatile VOCs evolve first. At longer times and/or higher temperatures, the larger, heavier, less volatile VOCs evolve. A similar but likely higher resolution result is achieved in laboratory gas chromatography.

Disclosed herein is a system and method to use multiple dimensions of analysis to capture a characteristic signature of a mixed gas species by pairing a sensor module, which has at least one sensor, with a preconcentrator module in a package with a single common air input port. Controlled heating of the preconcentrator allows for a limited volatility separation, which adds an additional axis of discrimination to a sensor array and potentially allows for measurement of much smaller concentrations by adsorbing gases for a long time and then releasing all, or most, at once. The use of a preconcentrator to provide limited chemical separation need not be limited to applications requiring a complete separation of a molecule for discrimination of a single molecular species. In an embodiment, the gas sensor is an array of metal oxide (MOX) sensors either operating at different temperatures or having different metal oxide coatings.

In various embodiments, the gas adsorbent material is a molecular sieve, porous carbon network, mesoporous silicon or silicon dioxide, zeolite, structured nanomaterial with high surface area, metal-organic framework, or porous or gas-absorbing polymer. The adsorption can be thermodynamically reversible below the melting temperature of the gas adsorbent material and its heater. The gas adsorbent material may be provided as a bulk sample, screened, jetted dispense, spin-on coating, spray-on coating from a dispersion, liquid dispensed with a binding agent as in an ink, or chemically grown or etched, patterned film transferred, or other effective technique.

In various embodiments, the one or more gas preconcentrator modules and the one or more gas sensor modules are mounted in a cavity of a combination package. In various embodiments, the package has an integral cover or lid, such as a metal mesh or grid, a gas permeable membrane such as silicone (e.g. PDMS) or partially sintered or expanded Teflon (PTFE) or water barrier (e.g., Gortex fabric), which passes gasses but not liquids for small pressure differentials. In various embodiments, the one or more gas preconcentrator modules are mounted in a first cavity of a combination package and the one or more gas sensor modules are mounted in a second cavity of the combination package, wherein the cavities are in fluid communication. In various embodiments, the one or more gas preconcentrator modules are mounted in a cavity of a first package and the one or more gas sensor modules are mounted in a cavity of a second package, wherein an exit port of the cavity of the first package is in fluid communication with an input port of the cavity of the second package. It can advantageous to limit the amount of surface area in the module as package surface area has a capacitive effect by capturing gases evolving from the preconcentrator and then releasing them later. Extraneous surface area can reduce the resolution of the volatility separation. It can also be advantageous to adjust the chemical resistance (diffusion rate) between an ambient source of gases, such as VOCs, and the gas characterization system. Lower diffusion offers higher signal gain by effectively trapping preconcentrated gases evolving from the heater. Higher diffusion offers less gain but faster preconcentrator loading and readout time. The diffusive chemical resistance to ambient can be controlled by selecting the porosity of a lid, which can also serve as or be in addition to a water barrier such as Gortex fabric or polymer membrane.

In various embodiments, the one or more gas sensor modules include a metal oxide gas sensor or array of metal oxide gas sensors. In other embodiments, the gas sensor modules includes individual elements or arrays of electro-chemical sensors, capacitive sensors with selective adsorbent coatings, gravimetric sensors such as MEMS resonators with selectively absorbing coatings, flame ionization detectors, ionic polymer-coated floating gate transistor detectors, color-change chemical sensors and readout imager, optical absorption-based sensor such as a non-dispersive infrared (IR) sensor, or the like.

In various embodiments, the one or more gas preconcentrator modules are in a first package having an input gas port exposed to ambient air and having a gas permeable membrane attached to the input gas port, where the one or more gas sensor modules are in a second package having an output gas port exposed to ambient air and having a second gas permeable membrane attached to the output gas port. In some embodiments, the first package and second package are optionally the same package.

In an embodiment, a gas sensor system includes a metal oxide gas sensor module. The module can include a substrate having a top surface and a bottom surface. A first part of the top surface has a gas adsorbent material attached to it and a first electrical heater element attached to a first part of the bottom surface opposite the first part of the top surface. A second part of the top surface has an interdigitated array of electrodes attached to it and a metal oxide coating attached to the second part of the top surface and covering the interdigitated array of electrodes. A second electrical heater element is attached to a second part of the bottom surface opposite the second part of the top surface.

In an embodiment, the gas sensor system includes an electrochemical sensor in which the working electrode bias is varied in time, as in cyclic voltammetry, or an electrochemical sensor array in which one or more working electrode biases are independently set or varied to obtain a chemical-dependent response. Additional discrimination is possible in electrochemical sensors via combinations of selective filters such as carbon filters, choice of electrolyte or ionic conductor and electrode material or coating.

In an embodiment, the one or more preconcentrators and gas sensors are monolithically fabricated, for example, using a MEMS silicon-based fabrication process for compactness and high volume manufacturability. In other embodiments, the preconcentrators can be fabricated from a separate wafer and pick-and-placed in the package next to a die having an array of MOX sensors. In other embodiments, all the sensors can be from unique die and affixed to the package using a die attachment. An integrated circuit can also be included in the package to control the preconcentrator and gas sensor temperatures and readout the gas sensors.

A method of analyzing a gas or air sample using a gas sensor system is also disclosed herein. The method can include providing a gas sensor system having an array of metal oxide gas sensor modules optionally with different chemical responses, where the array includes at least two modules. The method can also include providing a preconcentrator and heating it to evolve adsorbed gases. The method can further include setting each module at a first temperature. The method can further include reading electrical resistance of each MOX sensor. The method can further include incrementing each module to a second temperature, wherein the second temperature is different for at least two modules, wherein the step of incrementing is optionally decreasing or increasing temperature. Typically, the step is less than the temperature difference between the at least two modules. The method can further include reading electrical resistance of each module at the second temperature. The method can further include analyzing the resistance reading of each gas sensor module at each sensor second temperature and optionally interpolating the time-staggered array results into a full resolution time vs. temp responsivity map. If different MOX sensors are used, the response at the first temperature can be mapped on the 2D time vs. sensor map as one color and a derivative calculated from the difference of the two temperature measurements can be displayed as a second color.

Further disclosed herein is a method of analyzing a gas or air sample in two dimensions, such as volatility (e.g. boiling point) and reactivity (e.g. combustion temperature). The method can include providing a gas sensor system with a gas preconcentrator and a gas sensor array. The method can additionally include ramping or stepping the preconcentrator temperature. The smallest, lightest, most volatile gas species will evolve first. At higher temperatures heavier, larger, less volatile gas species can evolve from the preconcentrator. Thus, elevating the temperature of the preconcentrator can provide some chemical dispersion in time according to volatility or preconcentrator affinity. Taking a series of measurements from the sensor array as the preconcentrator temperature in incremented, the sensor array can obtain several snapshots of the chemical response. In an example implementation, the method provides a 2D scan or chemical fingerprint of analyte volatility and reactivity from a single temperature scan of the preconcentrator.

In some embodiments, the method includes providing a sensor array comprising MOX sensors at different operating temperatures. In some embodiments, the method includes providing a MOX sensor array, where the MOX sensor array can include MOX sensors with varied metal oxide materials for at least two different sensors. In some embodiments, the method includes providing a gas sensor system having one or more gas preconcentrator modules, where each preconcentrator module can include a substrate having a top surface having a gas adsorbent material attached to the top surface and having an electrical heater element and having one or more gas MOX sensor modules in fluid communication with the one or more gas preconcentrator modules. The method can also include providing a gas sensor system having one or more gas preconcentrator modules, where each preconcentrator module can includes a substrate having a top surface having a gas adsorbent material attached to the top surface and having an electrical heater element and having one or more gas MOX sensor modules in fluid communication with the one or more gas preconcentrator modules.

In some embodiments, the method further includes increasing temperature of at least one of the one or more gas preconcentrator modules from an initial preconcentrator temperature to a final preconcentrator temperature (micro-stepping) to increase the temperature resolution of the array. The method can also include increasing temperature of at least one of the one or more gas MOX sensor modules from an initial gas sensor temperature to a second gas temperature, wherein the increase of temperature of the at least one gas MOX sensor modules occurs during the period of increase of the temperature of the at least one gas preconcentrator modules, and wherein the cycle time of increasing the temperature of the at least one gas MOX sensor modules is at least two times the cycle time of increasing the temperature of the at least one preconcentrator modules.

Although temperature variation of MOX sensors is an exemplary embodiment, the gas analysis system and method disclosed herein pertains to a variety of gas sensors with a controllable selective property, and is particularly suited to sensors where the controllable property can be varied gradually or incrementally, including, but not limited to, electrochemical sensors (working electrode bias) and photoionization detectors (UV wavelength).

Example Implementations

FIG. 1A shows a top view of an embodiment of a gas sensor system 100A including a gas sensor module 206 and preconcentrator module 204 with at least one electrical line bundle 230 for heaters, electrodes, and other lines, including read lines. In an embodiment, the gas sensor system 100A includes a package 201 having a fixing surface 202. Preconcentrator module 204 and gas sensor module 206 are fixed to the fixing surface 202, which is optionally a cavity of package 201. The modules may have a distance 203 between them. An electrical line bundle 230 may include electrical lines on a printed circuit board (PCB).

Figure 1B:
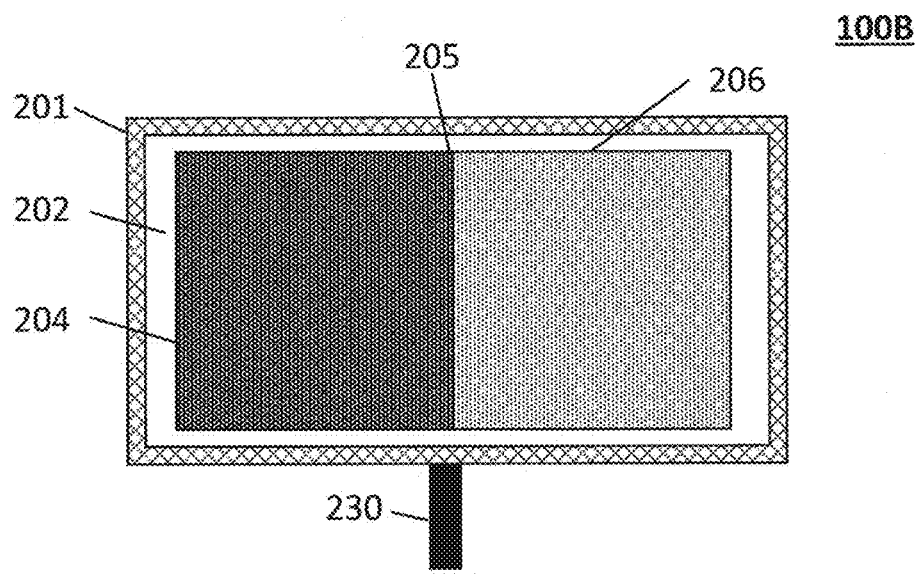
FIG. 1B illustrates a top view of a gas sensor and preconcentrator as one module and showing an electrical line bundle for heaters, electrodes, and other lines, including read lines, in accordance with an embodiment of this disclosure.

FIG. 1B shows a top view of an embodiment of a gas sensor system 100B including a gas sensor 206 and preconcentrator 204 as one module with at least one electrical line bundle 230 for heaters, electrodes, and other lines, including read lines. In an embodiment, the gas sensor system 100B includes a package 201 having a fixing surface 202. Preconcentrator module 204 and gas sensor module 206 are fixed within to the fixing surface 202, which is optionally a cavity of package 201. As shown, the preconcentrator and gas sensor modules can be combined into one module with no distance 205 between them. An electrical line bundle 230 may include electrical lines on a printed circuit board (PCB).

Figure 2A:
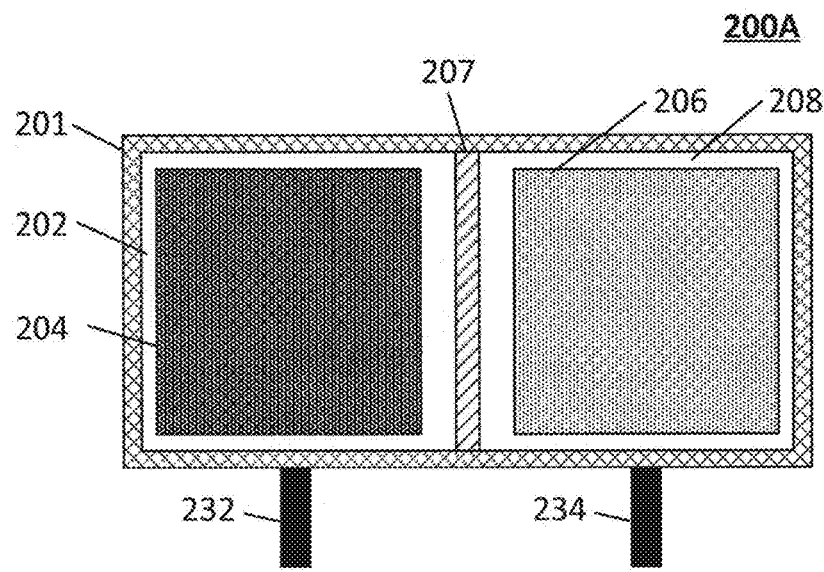
FIG. 2A illustrates a top view of a gas sensor module and preconcentrator module separated by a divider having a gas flow channel and showing electrical line bundles for heaters, electrodes, and other lines, including read lines, in accordance with an embodiment of this disclosure.

FIG. 2A shows a top view of and embodiment of a gas sensor system 200A including a gas sensor module 206 and preconcentrator module 204 separated by a divider 207 having a gas flow channel with electrical line bundles 232 and 234 for heaters, electrodes, and other lines, including read lines. In an embodiment, the gas sensor system 200A includes a package 201 having fixing surfaces 202 and 208. Preconcentrator module 204 is fixed to fixing surface 202, and gas sensor module 206 is fixed to the fixing surface 208. A divider 207 divides the package 201 into separate regions separating the two modules 204 and 206. The modules are in fluid communication (e.g., fluidically coupled) with one another. The modules are optionally in cavities of package 201. Electrical line bundles 232 and 234 may include electrical lines on a printed circuit board (PCB).

Figure 2B:
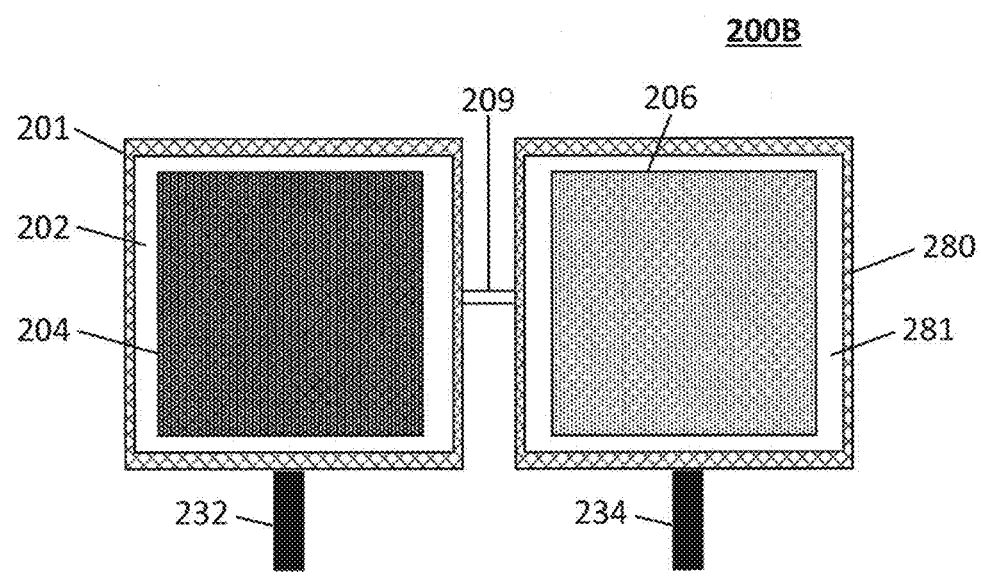
FIG. 2B illustrates a top view of a gas sensor module and a separate preconcentrator module connected by a gas flow line and showing electrical line bundles for heaters, electrodes, and other lines, including read lines, in accordance with an embodiment of this disclosure.

FIG. 2B shows a top view of and embodiment of a gas sensor system 200B including a gas sensor module 206 and a separate preconcentrator module 204 fluidically connected by a gas flow line 209 and having electrical line bundles 232 and 234 for heaters, electrodes, and other lines, including read lines. The gas sensor system 200B includes a package 201 having fixing surface 202 and package 280 having fixing surface 281. Preconcentrator module 204 is fixed to fixing surface 202, and gas sensor module 206 is fixed to the fixing surface 281. The modules are in fluid communication via line 209. The modules are optionally in cavities of package 201 and 280, respectively. Electrical line bundles 232 and 234 may include electrical lines on a printed circuit board (PCB).

Figure 3A:
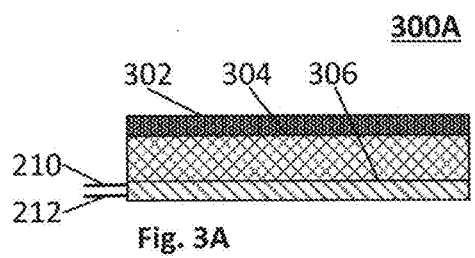
FIG. 3A illustrates a cross section of preconcentrator having a heater below a substrate having a coating of capture material on a top surface, in accordance with an embodiment of this disclosure.

FIG. 3A shows a cross section of a preconcentrator 300A in accordance with an embodiment of this disclosure. In an embodiment, the preconcentrator 300A includes a substrate 304 with a coating 302 of gas adsorbing material and having an electrical heater 306, with electrical lines 210 and 212, located below the substrate 304. The gas adsorbing material can be a molecular sieve material that is coated on the substrate 304 using any method in the art such as printing methods, spray methods, or blade coating methods, as well as methods to be devised.

Figure 3B:
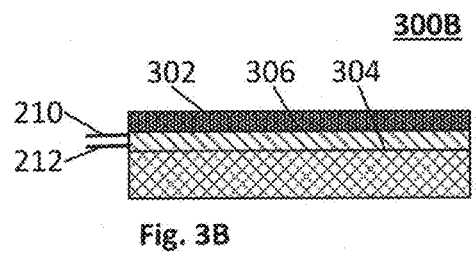
FIG. 3B illustrates a cross section of preconcentrator having a heater above a substrate having a coating of capture material on the heater and on a top surface of the substrate, in accordance with an embodiment of this disclosure.

FIG. 3B shows a cross section of a preconcentrator 300B in accordance with another embodiment of this disclosure. In an embodiment, the preconcentrator 300B includes a substrate 304 having an electrical heater 306, with electrical lines 210 and 212, located above the substrate 304. A coating 302 of gas adsorbing material can cover the substrate 304 and heater 306. The gas adsorbing material can be a molecular sieve material that is coated using any method in the art such as printing methods, spray methods, or blade coating methods, as well as methods to be devised.

Figure 3C:
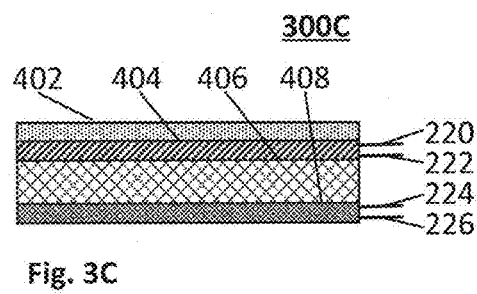
FIG. 3C illustrates a cross section of a typical MOX sensor having a heater on a bottom surface of a substrate, sense electrodes on a top surface of the substrate, and a MOX material on the top surface of the substrate and on the electrodes, in accordance with an embodiment of this disclosure.

FIG. 3C shows a cross section of an embodiment of a MOX sensor 300C having a heater 408 on a bottom surface of a substrate 406, sense electrodes 404 on a top surface of the substrate 406, and a MOX material 402 on the top surface of the substrate 406 and on the electrodes 404. MOX sensor 300C has a substrate 406 with heater 408, interdigitated electrodes 404, and MOX coating 402. Electrical lines 220 and 222 can connect the interdigitated electrodes 404 to a control system, and electrical lines 224 and 226 can connect the heater 408 to a control system.

Figure 3D:
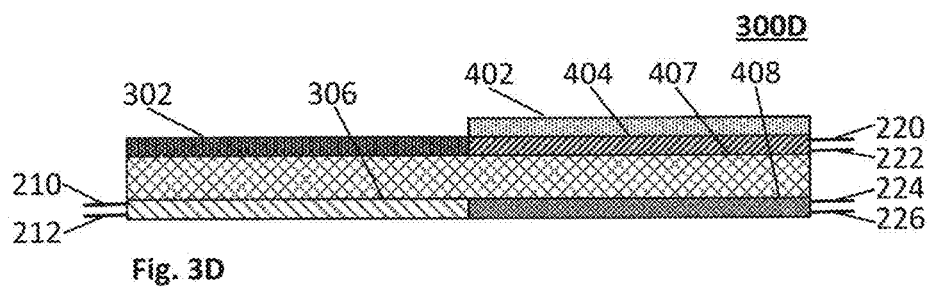
FIG. 3D illustrates a cross section of a MOX sensor and preconcentrator as a single module, wherein the heater for preconcentrator optionally can be on top surface or the bottom surface, in accordance with an embodiment of this disclosure.

FIG. 3D shows an embodiment a MOX sensor and preconcentrator as a single combined module 300D, where the heater 306 for preconcentrator optionally can be on the top surface or the bottom surface of a substrate 407. In an embodiment, the combined module 300D includes substrate 407, heater electrode 306 with electrical lines 210 and 212, heater electrode 408 with lines 224 and 226, interdigitated electrodes 404 with electrical lines 220 and 222, MOX material 402, and gas adsorbent material 302.

Figure 4:
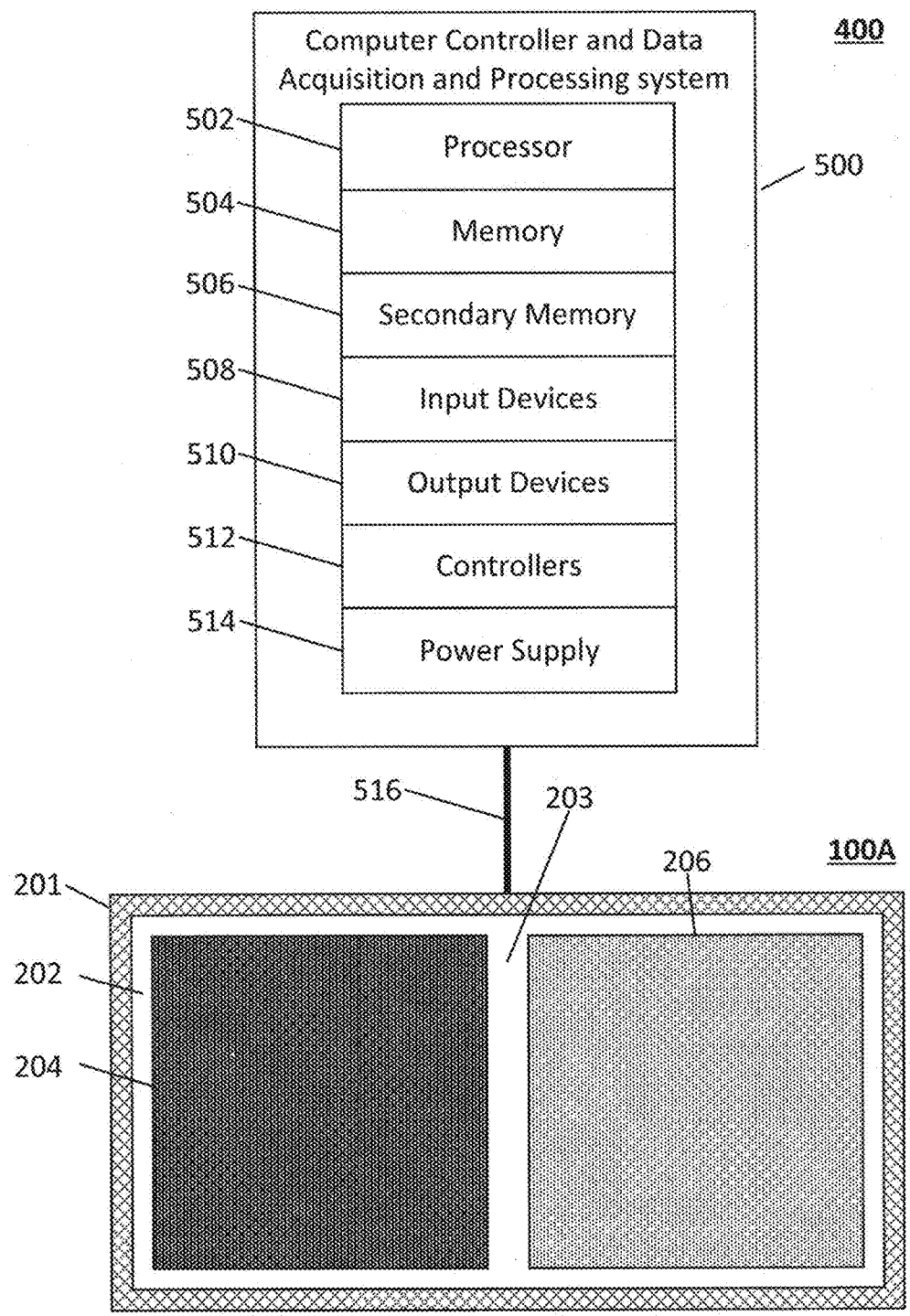
FIG. 4 illustrates a gas sensor and preconcentrator module controlled by a computer system, which can control, collect data, analyze data, and display results, as well as store all data and analyses and send results electronically, in accordance with an embodiment of this disclosure.

FIG. 4 illustrates an embodiment of a system 400 including a gas sensor 206 and a preconcentrator 204 controlled by a computer system or controller 500 configured to control, collect data, analyze data, display results, store data and analyses, send results electronically, and so forth. The gas sensor system 100A includes a package 201 having a fixing surface 202. Preconcentrator module 204 and gas sensor module 206 are fixed to the fixing surface 202, which is optionally a cavity of package 201. The modules may have a distance 203 between them or can be integrated into a combined module. At least one electrical line bundle 230 may include electrical lines on a printed circuit board (PCB) and connects to controller 500. Controller 500 may include a processor 502 and memory 504 including program instructions enabling the controller 500, upon execution of the program instructions, to carry out one or more operations or steps described herein. The controller 500 can also include a secondary memory 506, at least one input device/port 508, at least one output device/port 510, one or more sub-controllers 512, a power supply 514, and so forth. In some embodiments, the controller 500 can include or can be coupled with control circuitry (e.g., microprocessor or microcontroller) of a mobile device (e.g., a cellular smart phone, tablet, notebook, media player, smartwatch, or other mobile computing system).

Figure 5A:
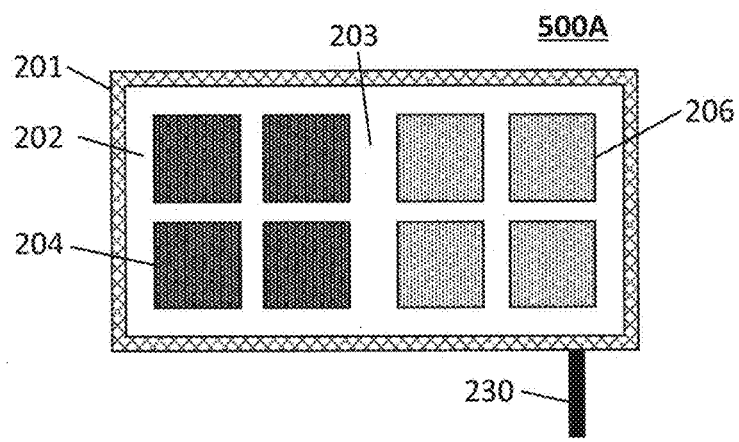
FIG. 5A illustrates a gas sensor and preconcentrator module having multiple units in an array, in accordance with an embodiment of this disclosure.

An embodiment of a gas sensor system 500A is shown in FIG. 5A to include a gas sensor 206 and a preconcentrator 204 distributed as multiple units or modules in respective arrays. In an embodiment, the system 500A includes a package 201 having an array of preconcentrator modules 204 fixed to a fixing surface 202 and an array of gas sensor modules 206 fixed to the fixing surface 202. A distance 203 may separate the preconcentrator array 204 and the gas sensor array 206, which are in fluid communication with one another. An electrical line bundle 230 may include electrical lines on a printed circuit board (PCB).

Figure 5B:
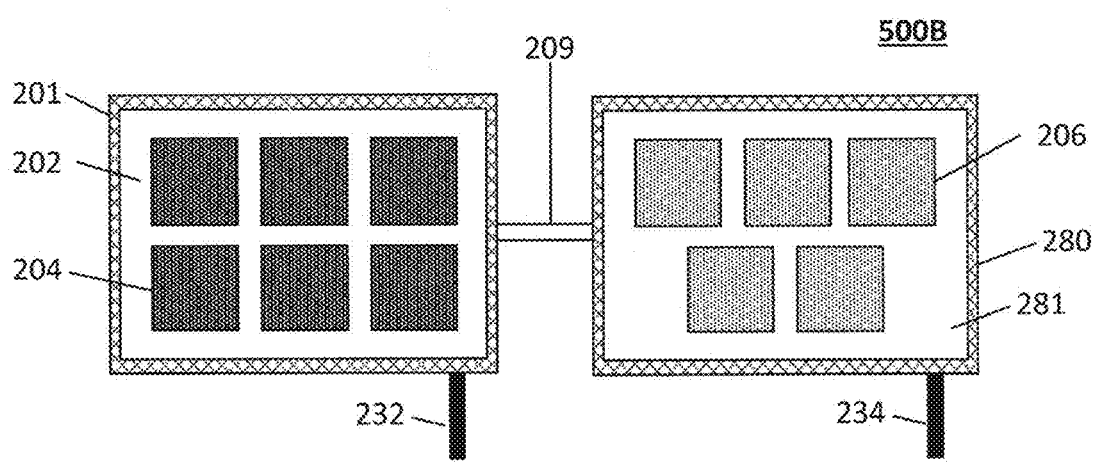
FIG. 5B illustrates a gas sensor module and separate preconcentrator module connected by a gas flow line and each having multiple units in an array, in accordance with an embodiment of this disclosure.

FIG. 5B shows another embodiment, where a gas sensor system 500B includes a gas sensor array and a separate preconcentrator array connected by a gas flow line 209. In an embodiment, the system 500B includes a package 201 having an array of preconcentrator modules 204 fixed to a fixing surface 202 and another package 280 having an array of gas sensors 206 fixed to a fixing surface 281. Gas line 209 provides fluid communication between each of the arrays. Electrical line bundles 232 and 234 may include electrical lines on a printed circuit board (PCB).

Figure 6A:
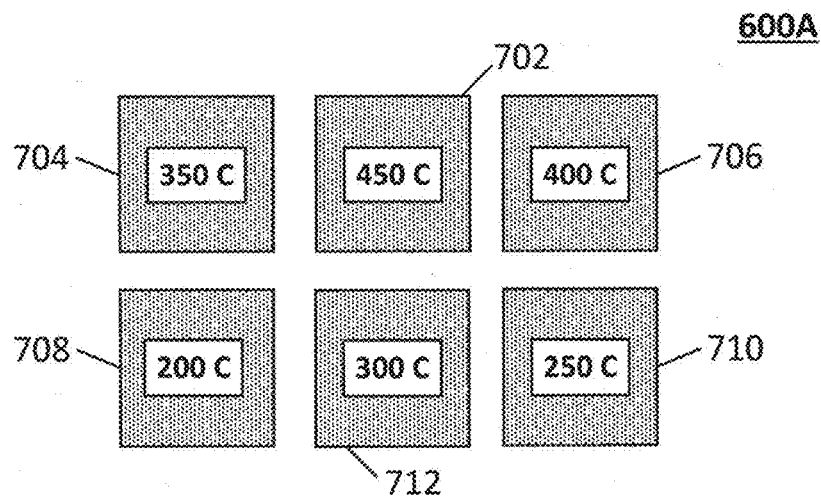
FIG. 6A illustrates an array of MOX gas sensor modules set at a first temperature, in accordance with an embodiment of this disclosure.

FIG. 6A shows an embodiment of an array 600A of MOX gas sensor modules with each module set at respective a first temperature. For example, the gas sensor array 600A can include, but is not limited to, six modules 702, 704, 706, 708, 710, and 712. For further example, the first temperature of each modules can be set as follows: module 708 at 200° C., module 710 at 250° C., module 712 at 300° C., module 704 at 350° C., module 706 at 400° C., and module 702 at 450° C. The difference in temperature between the modules is shown as 50° C.; however, is shall be understood that the foregoing first temperatures and module-to-module differences are examples and can be replaced by other temperatures which may be deemed necessary, convenient, or advantageous for a particular implementation. For example, the difference in temperature between the modules could be 5° C. or 10° C. As another example, the difference could be 100° C. As another example, the difference in temperature between each module could be a different increment between different modules such as 10° C. between two modules and 35° C. between one of those modules and another module in the array. As an example in the array of six modules, the first temperatures could be set at 194° C., 231° C., 285° C., 333° C., 395° C., and 442° C. These temperatures are all provided for explanatory purposes and to illustrate various embodiments. None of these example temperatures are intended as limitations of the present disclosure, unless otherwise specified in the claims.

At low temperatures, reactive species generate a change in resistance. As the temperature increases, less reactive species begin to react. As the MOX temperature changes, the reacting species spend less time on the MOX surface and the overall responsivity decreases. The rate of increase (reactivity) and decrease (sticking coefficient) provides a means for chemical selectivity. However, the amount of time required to scan a single sensor through the entire useful temperature range of the sensor can be limited by a surface equilibration time that can make such a temperature scan require up to several minutes to complete. With the gas sensor and preconcentrator modules configured as arrays, parallel collection of temperature-dependent responsivity is enabled. When the number of elements in the array is limited by power consumption or size constraints, incrementing or decrementing the temperature of the sensor arrays enables an increase of the effective temperature resolution by interpolation. Additionally, small temperature changes can equilibrate faster than larger ones. A small increment/decrement step can also be considered to provide a response and derivative response at each temperature point.

In some embodiments, controlling the temperature of the heater arrays can be achieved by controlling the current in the heaters. Additionally, the temperature can be estimated by measuring the resistance of the heater itself (not the sensor electrodes), as most heater materials have a temperature dependent resistance including metals and semiconductors. By measuring the resistance of the heater, it is possible to provide a closed-loop control of the module temperature. The resistance of the heaters can optionally be calibrated in automated test equipment, and the coefficients stored in an integrated circuit. The integrated circuit may also contain the heater resistance sense and current control functions, in addition to the sensor module sensor electrode resistance measurement functions. In some embodiments, the integrated circuit and sensor modules can be co-packaged.

Figure 6B:
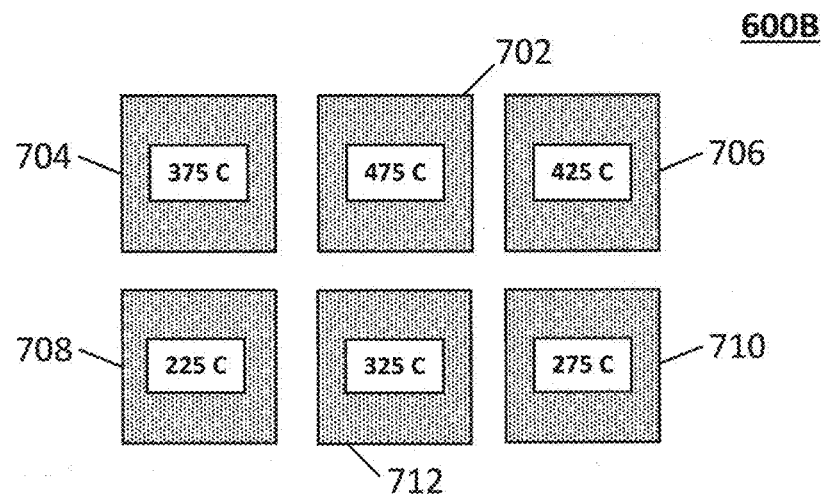
FIG. 6B illustrates an embodiment of an array of MOX gas sensor modules incremented to a second temperature as compared to FIG. 7A.

FIG. 6B shows an embodiment of an array 600B of MOX gas sensor modules with each module incremented to a second temperature as compared to a first temperature of the module (e.g., temperatures in FIG. 7A). For example, each module is shown as being incremented by 25° C. above its first temperature. Other increments can be used such as 4° C., 12° C., 36° C., 52° C., or any other appropriate temperature increment for each module. Additionally, different increments can be used for different modules, such as 5° C. for one module, 10° C. for another module, 30° C. for yet another module, and so forth. These temperatures and increments are all provided for explanatory purposes and to illustrate various embodiments. None of these example temperatures or increments are intended as limitations of the present disclosure, unless otherwise specified in the claims.

Figure 7:
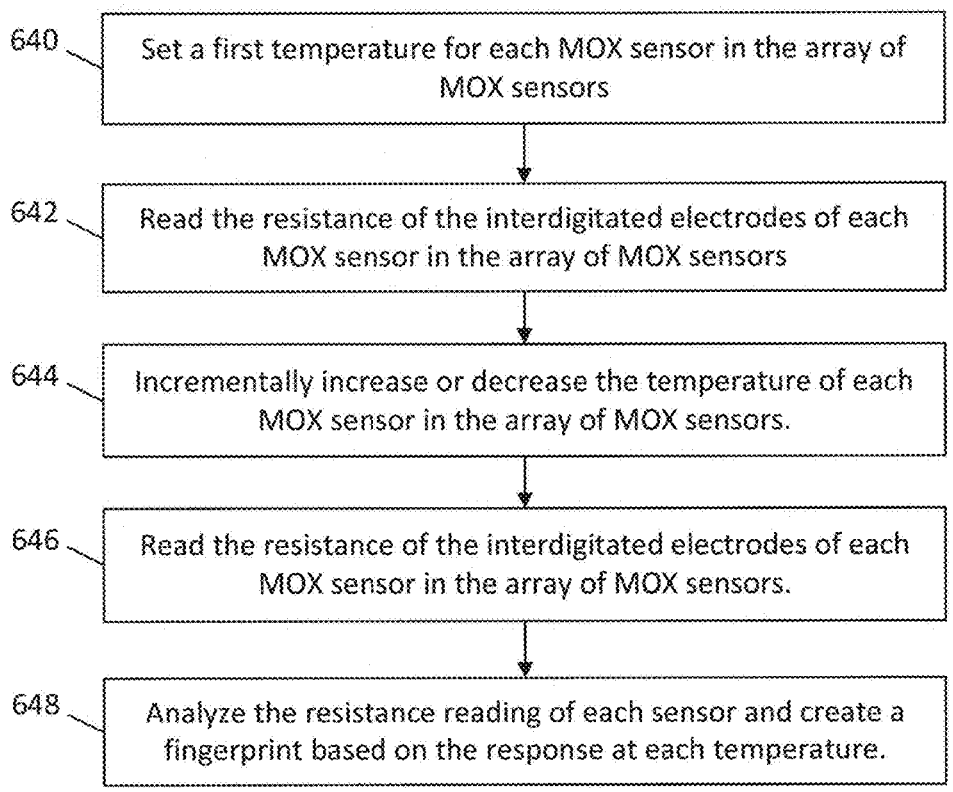
FIG. 7 illustrates an implementation of a method of parallel temperature acquisition of the resistance reading of each MOX gas sensor in an array of MOX gas sensors.

FIG. 7 illustrates a method 700 of parallel temperature acquisition of the resistance reading of each MOX gas sensor in an array of MOX gas sensors. At step 640, a first temperature can be set for each MOX sensor in an array of MOX sensors. At step 642, the resistance of each MOX sensor at the first temperature can be read or collected (e.g., via a controller coupled to the MOX sensors). At step 644, a heater element can be used to incrementally increase or decrease the temperature of each MOX sensor in the array of MOX sensors to a second temperature. At step 646, the resistance of each MOX sensor at the second temperature can be read or collected. At step 648, the resistance reading of each sensor can be analyzed to create a fingerprint (e.g., mathematical characterization) based on the response at each temperature. The measurements at each temperature can form an array of responses. The responses may be measured relative to the nominal resistance prior to preconcentrator heating.

Figure 8:
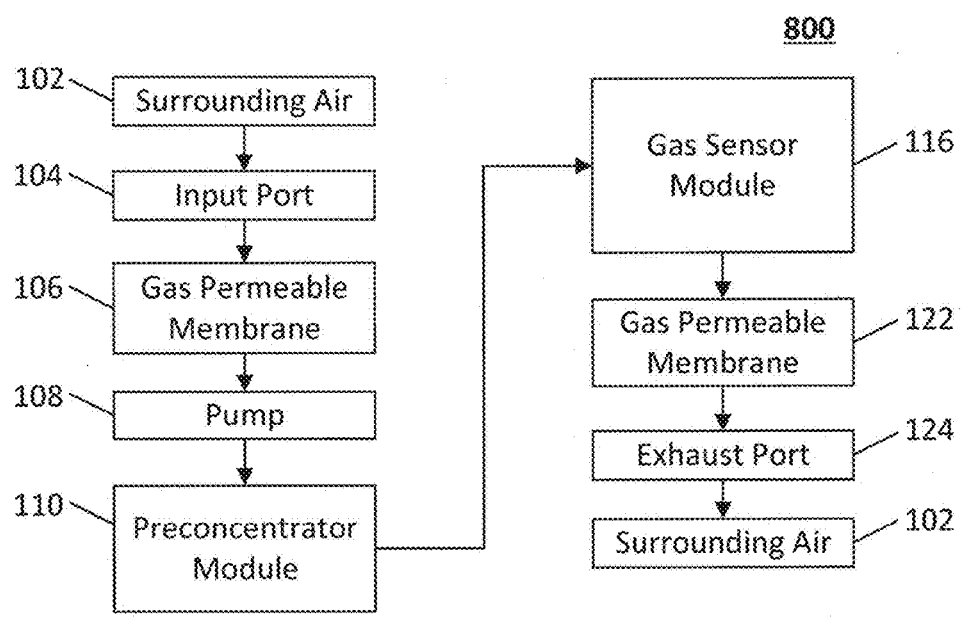
FIG. 8 shows flow of a gas sample through an embodiment of a gas sensor system with an optional pump, which can be on either side of the gas permeable membrane.

FIG. 8 illustrates flow of a gas sample through an embodiment of a gas sensor system 800 having an upstream pump, which can be on either side of the gas permeable membrane. In system 800, surrounding air 102 can pass through input port 104 to gas permeable membrane 106 and then through an optional pump 108 to a preconcentrator module 110, where certain gases attached to the gas adsorbent material in the module. The adsorbed gases are released from the preconcentrator module 110 when the module heater is turned on and then pass to the gas sensor module 116, where the gases are detected. The gases then pass through another gas permeable membrane 112 and pass out of exhaust port 124 back to surrounding air 102. In an embodiment, the exhaust port 124 is the same as the input port 104. Optionally, the pump may be a simple moveable diaphragm that creates a vacuum to draw in gas, thermal convection provided by a heater, or air agitation provided by an audio speaker.

Figure 9A:
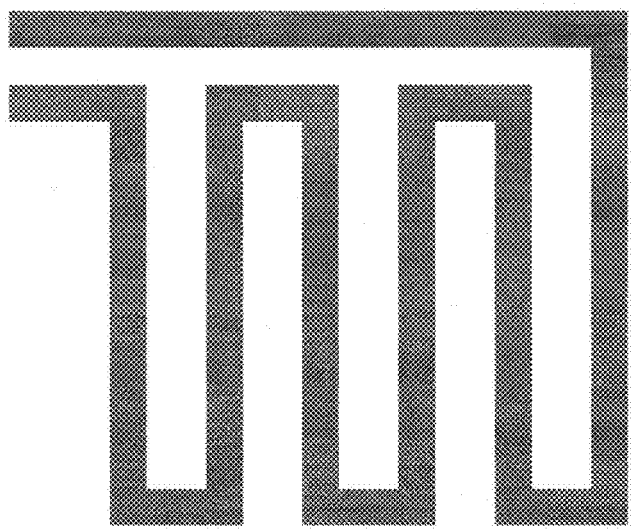
FIG. 9A illustrates a preconcentrator heater configuration, in accordance with an embodiment of this disclosure.
Figure 9B:
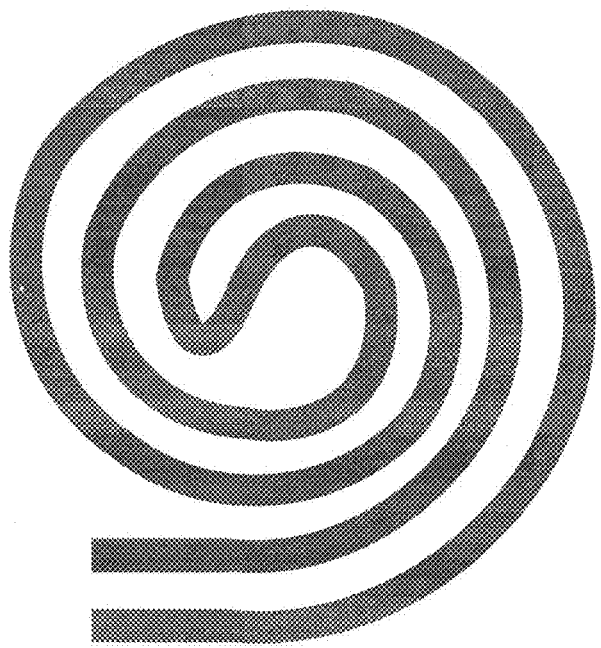
FIG. 9B illustrates a preconcentrator heater configuration, in accordance with an embodiment of this disclosure.

FIGS. 9A and 9B show example embodiments of preconcentrator heater configurations. Heater configuration 900A can include a simple rectangular heater structure, and configuration 900B can include a simple looped or coiled heater structure. Any simple or complex geometric shape may be used for the heater structure, as well as any combination of shapes. Other configurations can be used without departing from the scope of this disclosure.

Figure 10:
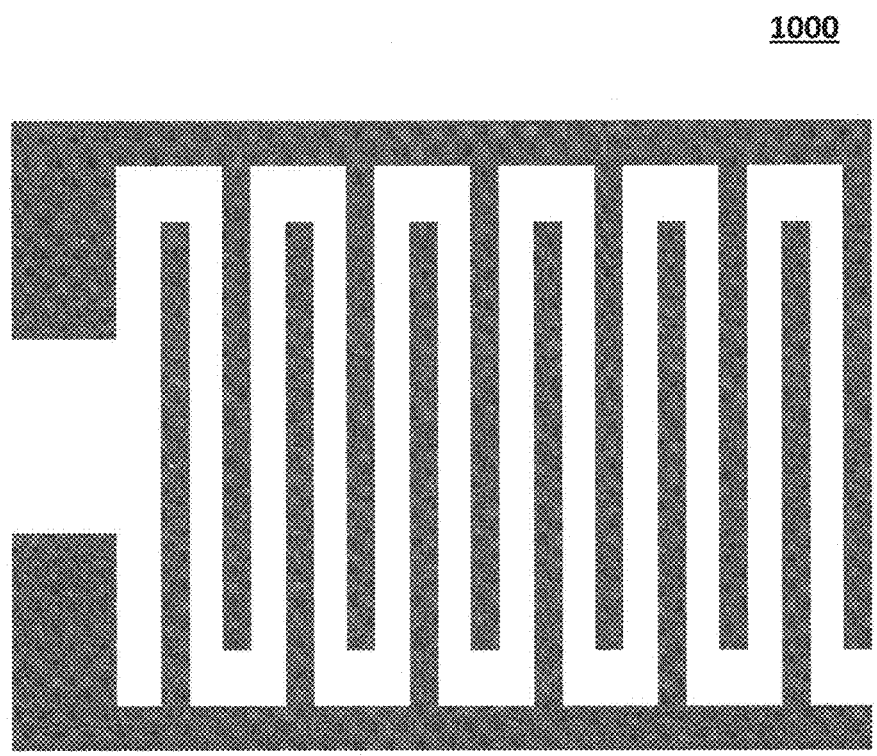
FIG. 10 illustrates an interdigitated electrode arrangement commonly used for MOX resistance readings, in accordance with an embodiment of this disclosure.

FIG. 10 shows an example embodiment of an interdigitated electrode arrangement 1000 commonly used for MOX resistance readings. The illustrated arrangement 1000 is a typical configuration used to measure resistance of a MOX coating. Other configurations can be used without departing from the scope of this disclosure.

Figure 11A:
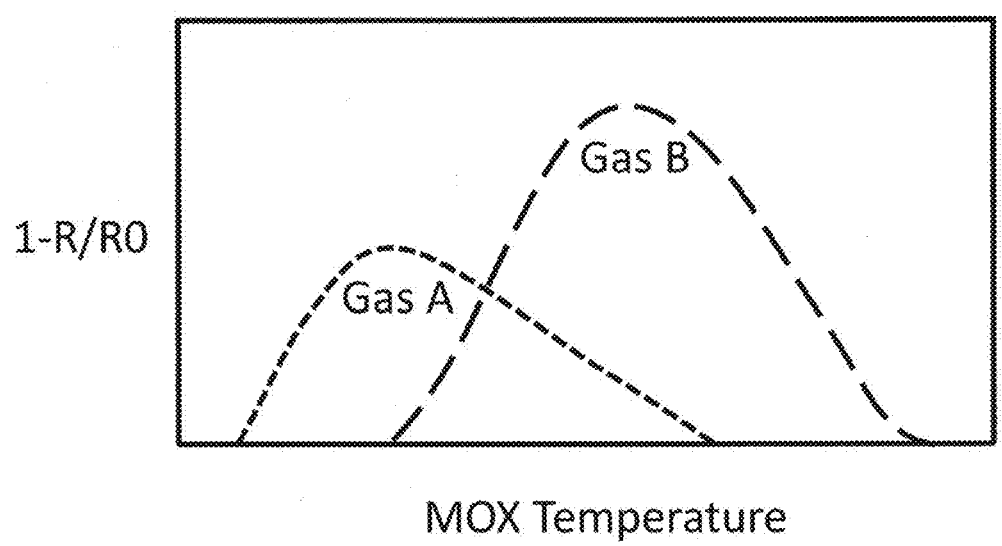
FIG. 11A provides a graph of a MOX temperature versus normalized MOX resistance for two different gases.
Figure 11B:
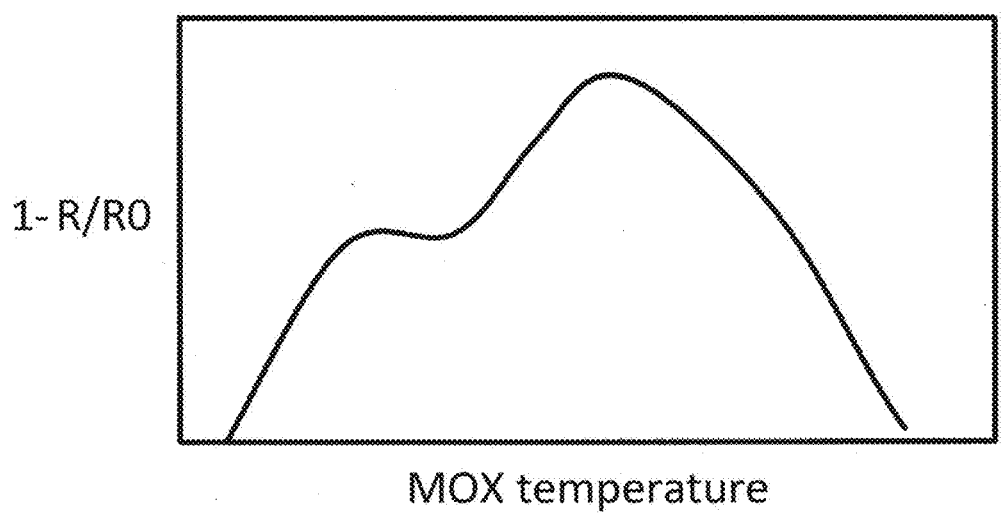
FIG. 11B provides a graph of a MOX temperature versus normalized MOX resistance, shown as a composite response of the two gases of FIG. 11A.

MOX sensors can have a characteristic temperature dependence based on the sensor and the gas species, as illustrated in FIG. 11A. FIG. 11A provides a plot of (1−R/R0) versus the temperature of a MOX sensor for two different gas species. R0 is the baseline resistance of the sensor, and R is the measured resistance during the temperature scan of the MOX sensor. The rising part of the curve can relate to a gas species reaching combustion temperature, and the falling slope can relate to a gas species not adsorbing long enough on the surface to combust. Gas A and Gas B have a characteristic curve for each species, and, as shown in the figure, the tail of the curve for Gas A overlaps with the rising portion of the curve for Gas B. For clarity, each curve is obtained separately from the gas sensor when each gas is contacted individually with the sensor. In a mixture of the gases, the curve may be a composite curve of the two curves, as shown in FIG. 11B. As can be seen in the composite curve, the individual gas species are only partially resolved. In some gas mixtures, there may be more overlap thus making resolution of individual gas species not possible with a MOX sensor.

Figure 12A:
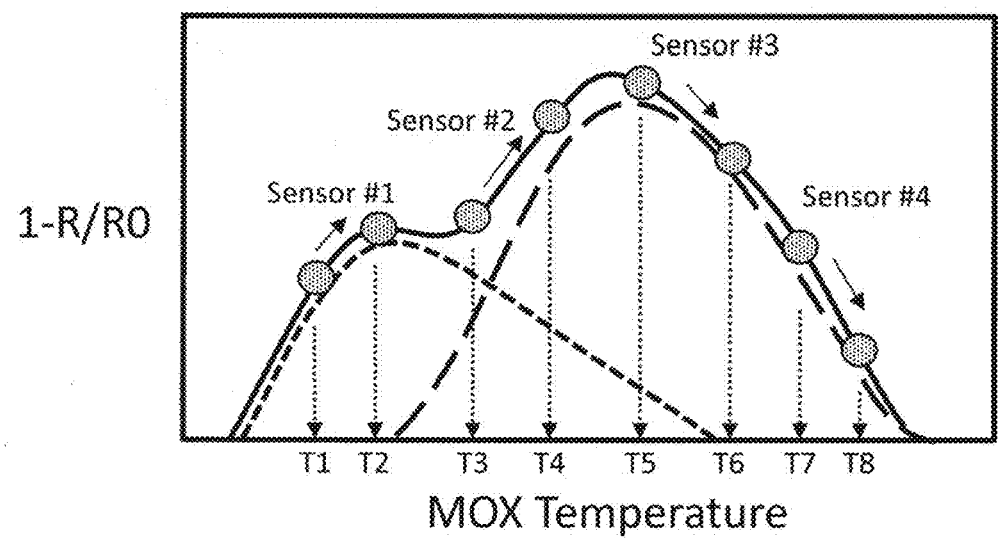
FIG. 12A provides a graph for two gases of a MOX temperature versus normalized MOX resistance for an array of MOX sensors, further shown as incremented from a first temperature to a second temperature, wherein the two gases are partially resolved in the composite response curve.
Figure 12B:
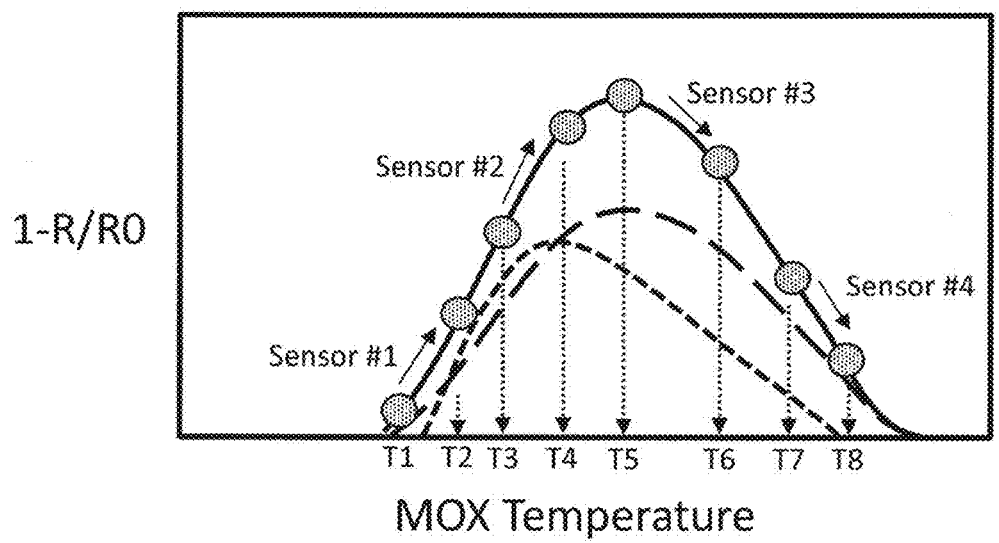
FIG. 12B provides a graph for two gases of a MOX temperature versus normalized MOX resistance for an array of MOX sensors, further shown as incremented from a first temperature to a second temperature, wherein the two gases are not resolved in the composite response curve.

An array of MOX sensors, such as shown in FIG. 5A and FIG. 5B, can be used to obtain a complete MOX temperature scan for a single gas species or a mixture of gas species to produce a curve as shown in FIG. 11A or FIG. 11B. Many more that four sensors can be packaged in an array format. Each sensor in an array is set at a specific temperature, as shown in FIG. 6A, for example, in the range from rising slope to falling slope for a gas species or a mixture of a gas species. Such an array arrangement can allow for faster data acquisition since an entire curve can be obtained by reading the resistance value of each sensor and constructing the curve from the values obtained from each sensor. In order to compensate for variations in R/R0 values from sensor to sensor, the temperature of each sensor can be incremented to a higher value or lower value, and then the response of each sensor can be measured at the new incremented value. This is illustrated in FIG. 12A, where a composite curve for two gas species is obtained at a first temperature for each sensor and then at a second temperature for each sensor, as shown by the arrows, shaded dots, and the respective temperatures. Only four sensors are shown in the figure; however, an array can contain more than four, such as six, eight, 12, 20, or more sensors. This method of incrementing temperature can provide higher resolution of the composite curve. In FIG. 12B, another composite curve is shown for a two gas species mixture using the same method of incrementing temperature of an array of sensors. As shown in the figure, the array of sensors is not able to resolve the curve because the curves overlap significantly of the two gas species.

Figure 13:
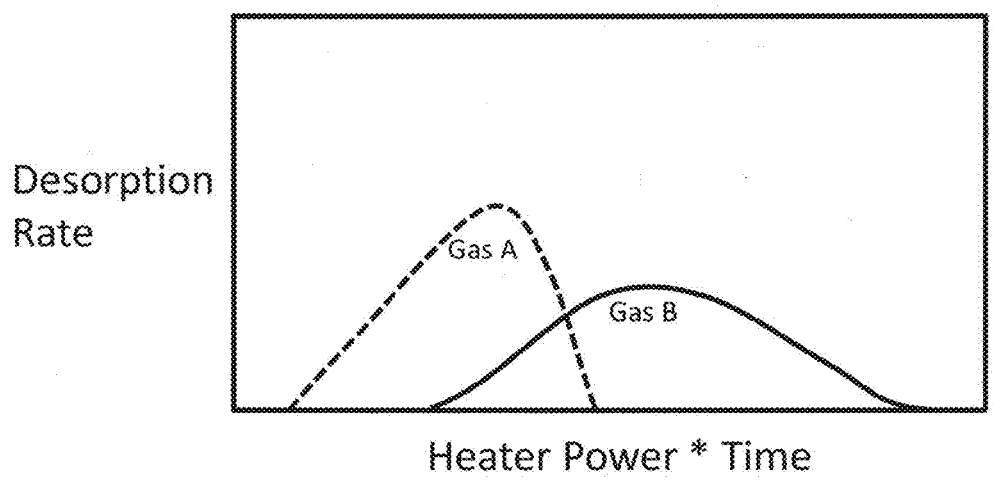
FIG. 13 provides a graph for two gases showing desorption rate of the gases from a preconcentrator as a function of heater power multiplied by time.

A preconcentrator adsorbs gas species and then, generally, releases the species according to volatility of each species. Release of the gas species from the preconcentrator may be a function of the amount of work done on the preconcentrator, where, for example, such work can be measured by heater power multiplied by time. Generally, gas species with less volatility evolve later than lighter species. This is illustrated in FIG. 13, wherein "lighter" Gas A evolves before "heavier" Gas B.

Figure 14A:
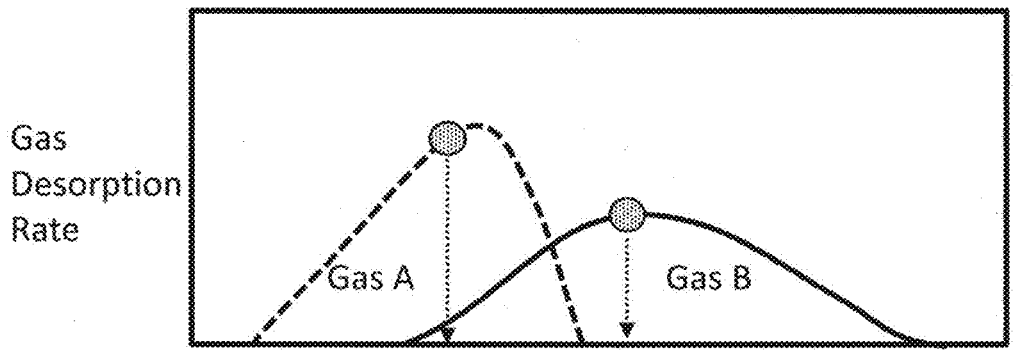
FIG. 14A provides a graph for two gases showing desorption rate of the gases from a preconcentrator as a function of heater power multiplied by time, wherein Time 1 is identified as near the peak desorption time for Gas A and Time 2 is identified as near the peak desorption time for Gas B.
Figure 14B:
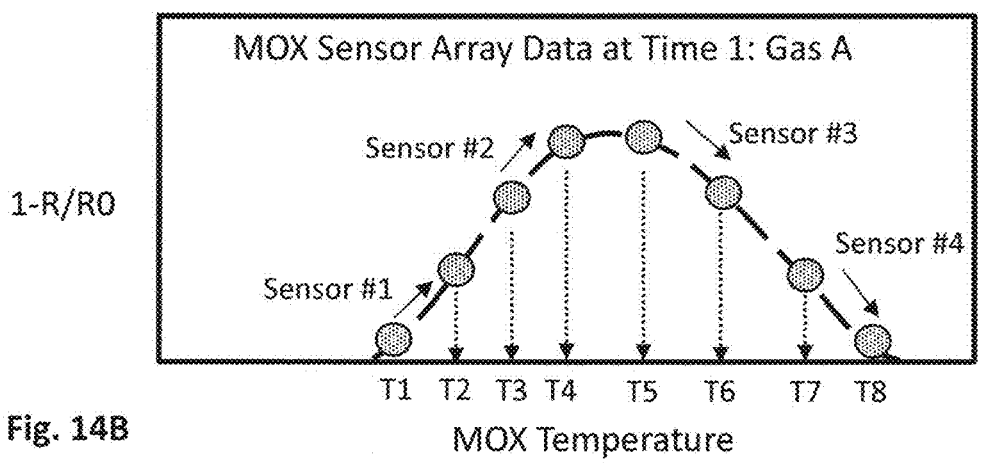
FIG. 14B provides a graph of MOX sensor array data taken at Time 1 corresponding to the peak desorption of Gas A in FIG. 14A and further shows incrementing the sensor temperature for each sensor at Time 1 to obtain further detail of the data curve.

A gas mixture of A and B as shown in FIG. 12B where a MOX sensor cannot resolve the different species can be resolved using a preconcentrator with a MOX sensor array, provided that the two gases have preconcentrator desorption curves that are relatively distinct from each other as illustrated in FIG. 14A. In FIG. 14A, the gases are shown as desorbing at a certain rate as a function of the preconcentrator heater on-time. As time increases, Gas A desorbs first, followed by Gas B. There is some overlap of the curves. The MOX sensor array is sampled at Time 1, which corresponds to about the peak desorption rate for Gas A. Therefore, the signal from each sensor in the array of sensors will be predominately from Gas A. The array data is illustrated in FIG. 14B for Gas A, with data from four sensors noted. In addition, FIG. 14B illustrates sensor data at Time 1 plus an incremental time to reach the new temperature for the sensor array (i.e., T1 to T2 for Sensor #1). This incrementing of the temperature allows further resolution of the curve.

Figure 14C:
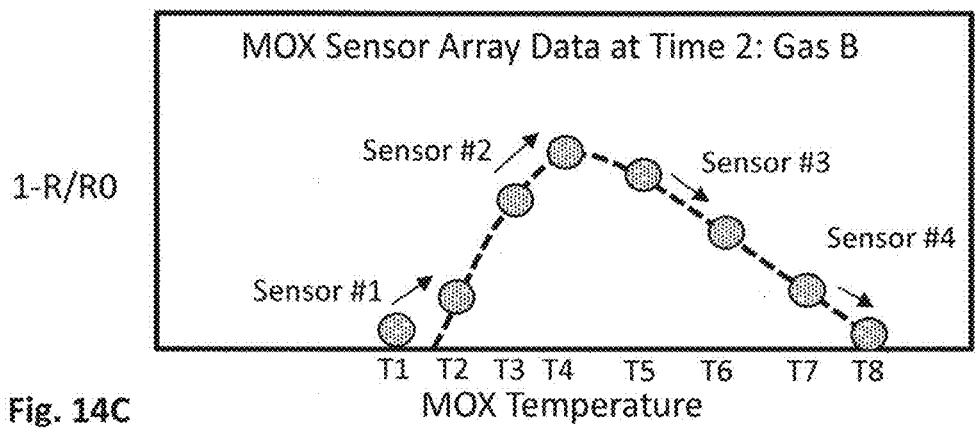
FIG. 14C provides a graph of MOX sensor array data taken at Time 2 corresponding to the peak desorption of Gas B in FIG. 14A and further shows incrementing the sensor temperature for each sensor at Time 2 to obtain further detail of the data curve.

Similarly, the sensor array is sampled at Time 2, which corresponds to about the peak desorption rate for Gas B. Therefore, the signal from each sensor in the array of sensors will be predominately from Gas B. The array data is illustrated in FIG. 14C for Gas B, with data from four sensors noted. In addition, FIG. 14C illustrates sensor data at Time 2 plus an incremental time to reach the new temperature for the sensor array (i.e., T1 to T2 for Sensor #1). This incrementing of the temperature allows further resolution of the curve.

Figure 15A:
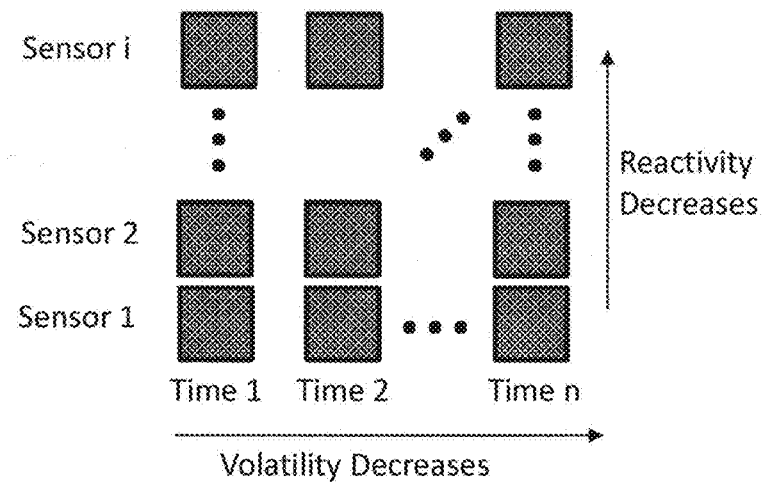
FIG. 15A provides a schematic of arranging data from a sensor array to obtain a two dimensional map or fingerprint of a gas or gas mixture.

A two-dimensional chemical mapping of a gas mixture can be done using a preconcentrator and an array of MOX sensors. This can be done by setting the sensors of the array at progressively higher temperature starting from the first sensor in the array being at the lowest temperature and the last sensor being set at the highest temperature. This arrangement allows for data to be collected on a gas or gas mixture over a range of temperatures of the array, as the gas is desorbed from the preconcentrator. Thus, the signal will vary from sensor to sensor with a peak as a sensor corresponding to the peak combustion temperature for that gas. This procedure can then be repeated at subsequent times to produce data on each sensor as a function of time. A plot can be made of the signal at each sensor as a function of time in a two dimensional array format, as illustrated in FIG. 15A. The two-dimensional array plot generally shows species with decreasing volatility on the time axis and species with decreasing reactivity on the sensor axis, with the lowest temperature sensor at the bottom. For example, a volatile, less reactive molecule can include $CH_3$. An example of a less volatile, more reactive molecule can include acetone. The values in the matrix are normalized to time 0 resistance since MOX sensors provide a ratiometric response.

Figure 15B:
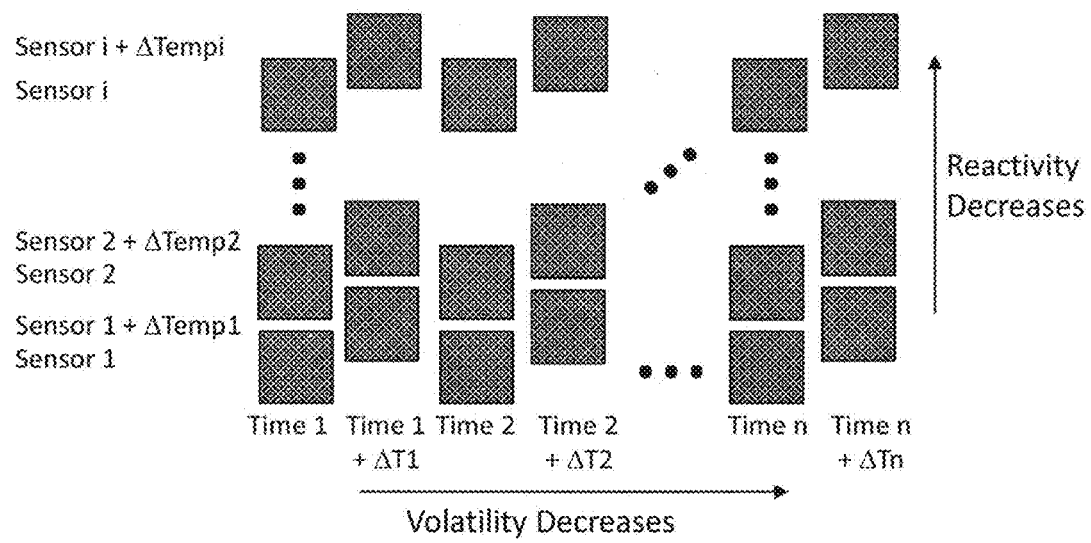
FIG. 15B provides a schematic of arranging data from a sensor array to obtain a two dimensional map or fingerprint of a gas or gas mixture, wherein further detail of the gas or gas mixture is obtain by incrementing sensor temperatures at each time point.

In order to obtain further two-dimensional mapping data, the MOX sensors can be incremented in temperature at each data collection time as illustrated in FIG. 15B. As described above, the sensor array responses can be arrange according to the order of the sensor for the y-axis and the time samples are arranged in the x-axis, providing an array of i-sensors and n-times. However, between each time series, the sensor array temperature is incremented as shown in FIG. 15B, the sensors are sampled as the incremental temperature, and then the temperature of each sensor is returned to the original temperature. The map obtained with temperature shifted data can be either interpolated onto a 2i×n×2n matrix, or else the derivatives obtained for each data point and displayed as a multicolor, forming a multicolor image. When the sensors have different MOX materials, temperature derivatives can be added as an additional dimension or color. Notably, if the temperature shifts are small, the material need not reach equilibrium for a useful derivative to be obtained, so the sample rate is not limited by an equilibration time.

It should be recognized that the various functions, operations, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, or any other device known in the art. In general, the terms "controller" and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed. Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A gas sensor system, comprising:
one or more gas preconcentrator modules, each gas preconcentrator module including a substrate having a top surface with a gas adsorbent material attached to the top surface and further including an integral electrical heater element; and
a plurality of gas sensor modules in fluid communication with the one or more gas preconcentrator modules, wherein the plurality of gas sensor modules includes at least a first gas sensor module with a first chemical responsiveness and a second gas sensor module with a second chemical responsiveness different from the first chemical responsiveness,
wherein the one or more gas preconcentrator modules are in a first package having an input gas port exposed to ambient air and having a gas permeable membrane attached to the input gas port, wherein the plurality of gas sensor modules are in a second package having an output gas port exposed to ambient air and having a second gas permeable membrane attached to the output gas port.

2. The gas sensor system of claim 1, wherein the gas adsorbent material is a molecular sieve.

3. The gas sensor system of claim 1, further comprising an integrated circuit in electrical communication with the preconcentrator and gas sensor modules.

4. The gas sensor system of claim 1, wherein the different chemical responsivities are obtained by operating similar metal oxide gas sensors at different temperatures.

5. The gas sensor system of claim 1 wherein the different chemical responsivities are obtained from metal oxide sensors with different metal oxide materials.

6. The gas sensor system of claim 1, wherein the one or more gas preconcentrator modules are mounted in a cavity of the first package and the plurality of gas sensor modules are mounted in a cavity of the second package, and wherein an exit port of the cavity of the first package is in fluid communication with an input port of the cavity of the second package.

7. The gas sensor of system 1, wherein the first package and second package are the same package.

8. The gas sensor system of claim 1, wherein the plurality of gas sensor modules comprise electrochemical gas sensors with differing chemical responsivities provided by differing working electrode potentials, filters, electrolytes or electrode materials.

9. The gas sensor system of claim 8, wherein at least one electrochemical gas sensor includes: a substrate having a top surface and a bottom surface, wherein a first part of the top surface has a gas adsorbent material attached thereto and a first electrical heater element attached to a first part of the bottom surface opposite the first part of the top surface, wherein a second part of the top surface has an interdigitated array of electrodes attached thereto and a metal oxide coating attached to the second part of the top surface and covering the interdigitated array of electrodes, and wherein a second electrical heater element is attached to a second part of the bottom surface opposite the second part of the top surface.

10. A gas sensor system, comprising:
one or more gas preconcentrator modules, each gas preconcentrator module including a substrate having a top surface with a gas adsorbent material attached to the top surface and further including an integral electrical heater element; and
a plurality of gas sensor modules in fluid communication with the one or more gas preconcentrator modules, wherein the plurality of gas sensor modules includes at least a first gas sensor module with a first chemical responsiveness and a second gas sensor module with a second chemical responsiveness different from the first chemical responsiveness,
wherein the plurality of gas sensor modules comprise electrochemical gas sensors with differing chemical responsivities provided by differing working electrode potentials, filters, electrolytes or electrode materials, and
wherein at least one electrochemical gas sensor includes:
a substrate having a top surface and a bottom surface, wherein a first part of the top surface has a gas adsorbent material attached thereto and a first electrical heater element attached to a first part of the bottom surface opposite the first part of the top surface, wherein a second part of the top surface has an interdigitated array of electrodes attached thereto and a metal oxide coating attached to the second part of the top surface and covering the interdigitated array of electrodes, and wherein a second electrical heater element is attached to a second part of the bottom surface opposite the second part of the top surface.

11. The gas sensor system of claim 10, wherein the gas adsorbent material is a molecular sieve.

12. The gas sensor system of claim 10, wherein the one or more gas preconcentrator modules and the plurality of gas sensor modules are mounted in a cavity of a combination package.

13. The gas sensor system of claim 10, further comprising an integrated circuit in electrical communication with the preconcentrator and gas sensor modules.

14. The gas sensor system of claim 10, wherein the different chemical responsivities are obtained by operating similar metal oxide gas sensors at different temperatures.

15. The gas sensor system of claim 10 wherein the different chemical responsivities are obtained from metal oxide sensors with different metal oxide materials.

16. The gas sensor system of claim 10, wherein the one or more gas preconcentrator modules are mounted in a first cavity of a combination package and the plurality of gas sensor modules are mounted in a second cavity of the combination package, wherein the cavities are in fluid communication with one another.

17. The gas sensor system of claim 10, wherein the one or more gas preconcentrator modules are mounted in a cavity of a first package and the plurality of gas sensor modules are mounted in a cavity of a second package, and wherein an exit port of the cavity of the first package is in fluid communication with an input port of the cavity of the second package.

18. The gas sensor system of claim 10, wherein the one or more gas preconcentrator modules are in a first package having an input gas port exposed to ambient air and having a gas permeable membrane attached to the input gas port, wherein the plurality of gas sensor modules are in a second package having an output gas port exposed to ambient air and having a second gas permeable membrane attached to the output gas port.

19. The gas sensor of system 18, wherein the first package and second package are the same package.

\* \* \* \* \*